(12) United States Patent  (10) Patent No.: US 9,180,232 B2
Williams et al.  (45) Date of Patent: Nov. 10, 2015

(54) SURGICAL SYSTEM HAVING MANIFOLDS WITH INTEGRAL PNEUMATIC ACCUMULATORS

(75) Inventors: David L. Williams, Newport Beach, CA (US); Michael Bowman, Fullerton, CA (US)

(73) Assignee: NOVARTIS AG, Basel (CH)

( * ) Notice: Subject to any disclaimer, the term of this patent is extended or adjusted under 35 U.S.C. 154(b) by 819 days.

(21) Appl. No.: 11/455,490

(22) Filed: Jun. 19, 2006

(65) Prior Publication Data

US 2007/0270735 A1   Nov. 22, 2007

Related U.S. Application Data

(63) Continuation-in-part of application No. 11/437,301, filed on May 19, 2006.

(51) Int. Cl.
*A61M 1/00* (2006.01)
*A61F 9/007* (2006.01)

(52) U.S. Cl.
CPC .......... *A61M 1/0058* (2013.01); *A61F 9/00736* (2013.01); *A61M 2205/123* (2013.01)

(58) Field of Classification Search
USPC ............. 137/271, 884; 417/477.2; 604/27, 35
See application file for complete search history.

(56) References Cited

U.S. PATENT DOCUMENTS

| | | | |
|---|---|---|---|
| 2,834,368 A * | 5/1958 | Gray | 137/271 |
| 3,654,960 A | 4/1972 | Kiernan | |
| 3,680,589 A * | 8/1972 | Jeans et al. | 137/884 |
| 3,823,714 A | 7/1974 | Waysilk et al. | |
| 3,823,724 A | 7/1974 | Davis | |
| 4,171,559 A * | 10/1979 | Vyse et al. | 29/407.01 |
| 4,230,143 A | 10/1980 | Dettmann et al. | |
| 4,395,258 A | 7/1983 | Wang et al. | |
| 4,493,695 A | 1/1985 | Cook | |
| 4,627,833 A | 12/1986 | Cook | |
| 4,735,610 A | 4/1988 | Akkas et al. | |
| 4,758,238 A | 7/1988 | Sundblom et al. | |
| 4,770,654 A | 9/1988 | Rogers et al. | |

(Continued)

FOREIGN PATENT DOCUMENTS

| | | |
|---|---|---|
| EP | 0095926 | 12/1983 |
| EP | 0888788 | 1/1999 |

(Continued)

OTHER PUBLICATIONS

"Manifold." The Free Dictionary by Farlex. Accessed online Jun. 24, 2013. <http://www.thefreedictionary.com/manifold>.*

(Continued)

*Primary Examiner* — Scott Medway
(74) *Attorney, Agent, or Firm* — Darien Reddick (57) ABSTRACT

A surgical system having all of the various pneumatic control sub-systems or sub-manifolds integrally mounted on a common primary manifold. The various required control mechanisms such as valves are likewise integrally mounted to the common manifold and to the sub-manifolds. Within any or all of the sub-manifolds or primary manifolds, volumes of material not necessary for the operation of the manifold are carved or pocketed out and used to form integral accumulators for storing extra pressurized air. The volume of the accumulator can vary according to the pressurized air requirement of the particular manifold, or the overall pneumatic system.

20 Claims, 6 Drawing Sheets

(56) References Cited

U.S. PATENT DOCUMENTS

| | | | |
|---|---|---|---|
| 4,904,168 A * | 2/1990 | Cavoto et al. | 417/477.2 |
| 4,963,131 A * | 10/1990 | Wortrich | 604/34 |
| 5,107,899 A | 4/1992 | Murphy | |
| 5,163,900 A | 11/1992 | Wortrich | |
| 5,282,787 A | 2/1994 | Wortrich | |
| 5,417,246 A | 5/1995 | Perkins et al. | |
| 5,499,969 A | 3/1996 | Beuchat et al. | |
| 5,549,139 A | 8/1996 | Perkins et al. | |
| 5,642,756 A * | 7/1997 | Lawrence et al. | 137/884 |
| 5,699,834 A * | 12/1997 | Hayashi et al. | 137/884 |
| 5,855,229 A * | 1/1999 | Gluf, Jr. | 137/884 |
| 5,857,485 A * | 1/1999 | Perkins et al. | 137/487.5 |
| 5,915,409 A * | 6/1999 | Kaneko et al. | 137/270 |
| 5,979,494 A | 11/1999 | Perkins et al. | |
| 6,102,068 A * | 8/2000 | Higdon et al. | 137/341 |
| 6,186,161 B1 * | 2/2001 | Hiramatsu | 137/271 |
| 6,197,197 B1 * | 3/2001 | Peterson et al. | 210/646 |
| 6,251,113 B1 | 6/2001 | Appelbaum et al. | |
| 6,561,999 B1 | 5/2003 | Nazarifar et al. | |
| 6,599,277 B2 | 7/2003 | Neubert | |
| 6,648,020 B2 | 11/2003 | Fujimoto et al. | |
| 6,824,525 B2 | 11/2004 | Nazarifar et al. | |
| 6,834,669 B2 | 12/2004 | Seyfarth | |
| 7,004,727 B2 * | 2/2006 | Kline et al. | 417/46 |
| 7,082,262 B2 | 7/2006 | Clark et al. | |
| 7,204,273 B1 | 4/2007 | Zub et al. | |
| 7,238,164 B2 * | 7/2007 | Childers et al. | 604/6.11 |
| 7,244,240 B2 | 7/2007 | Nazarifar et al. | |
| 2004/0124157 A1 | 7/2004 | Briggs et al. | |
| 2004/0195537 A1 | 10/2004 | Weber et al. | |
| 2005/0234441 A1 | 10/2005 | Bisch et al. | |

FOREIGN PATENT DOCUMENTS

| | | |
|---|---|---|
| EP | 1091130 | 4/2001 |
| EP | 1568339 | 8/2005 |
| JP | 2-286160 | 11/1990 |
| WO | WO 2004/060449 | 7/2004 |

OTHER PUBLICATIONS

European Search Report for Application No. 07108391.9, Publication No. 1857084, Published Nov. 21, 2007, 2 pages.
European Search Report for Application No. 07108390.1, Publication No. 1857128, Published Nov. 21, 2007, 2 pages.
European Search Report for Application No. 07108294.5, Publication No. 1857083, Published Nov. 21, 2007, 2 pages.
Unknown. Pneumatic Pinch Valves, *Sep. 2, 2004. ACRO Associates, Inc. <<http://www.acroassociates.com/products/pneumatic.html>>. Accessed Apr. 16, 2008, 3 pages.
Unknown. Internet Archive WayBack Machine. <<http://web.archive.org/web/*/www.acroassociates.com/products/pneumatic.html>>. Accessed Apr. 16, 2008, 1 page.

* cited by examiner

SURGICAL SYSTEM HAVING MANIFOLDS WITH INTEGRAL PNEUMATIC ACCUMULATORS

This application is a continuation-in-part application of U.S. patent application Ser. No. 11/437,301, filed May 19, 2006.

BACKGROUND OF THE INVENTION

The present invention relates generally to surgical systems and more specifically to surgical systems that control pneumatic devices.

Many microsurgical procedures require precision cutting and/or removal of various body tissues. For example, certain ophthalmic surgical procedures require the cutting and/or removal of the vitreous humor, a transparent jelly-like material that fills the posterior segment of the eye. The vitreous humor, or vitreous, is composed of numerous microscopic fibers that are often attached to the retina. Therefore, cutting and removal of the vitreous must be done with great care to avoid traction on the retina, the separation of the retina from the choroid, a retinal tear, or, in the worst case, cutting and removal of the retina itself.

Conventional vitrectomy probes typically include a hollow outer cutting member, a hollow inner cutting member arranged coaxially with and movably disposed within the hollow outer cutting member, and a port extending radially through the outer cutting member near the distal end thereof. Vitreous humor is aspirated into the open port, and the inner member is actuated, closing the port. Upon the closing of the port, cutting surfaces on both the inner and outer cutting members cooperate to cut the vitreous, and the cut vitreous is then aspirated away through the inner cutting member. This cutting action may be made using an electric cutter, but pneumatically driven probes operating at a relatively high pressure are more common.

Additionally, during typical ophthalmic procedures, air or other fluid may be introduced into the posterior chamber. This air must be of relatively low pressure (on the order of 3-4 psi). As the infusion of fluids into an eye is done at low pressures, this portion of the surgical procedure can extend for some period of time, so to protect against an unexpected loss in power, accumulation of some reserve pressure is desirable. Prior art devices have used pressure accumulators, receivers or tanks to store this reserve pressure. Such devices can occupy a great deal of space inside the surgical console and require pneumatic connection to the appropriate manifold.

Accordingly, a need continues to exist for a surgical system having a simplified, compact construction.

BRIEF SUMMARY OF THE INVENTION

The present invention improves upon prior art by providing a surgical system having all of the various pneumatic control sub-systems or sub-manifolds integrally mounted on a common primary manifold. The various required control mechanisms such as valves are likewise integrally mounted to the common manifold and to the sub-manifolds. Within any or all of the sub-manifolds or primary manifolds, volumes of material not necessary for the operation of the manifold are carved or pocketed out and used to form integral accumulators for storing extra pressurized air. The volume of the accumulator can vary according to the pressurized air requirement of the particular manifold, or the overall pneumatic system.

One objective of the present invention is to provide a surgical system having integrated pneumatic sub-systems.

Another objective of the present invention is to provide a surgical system having pneumatic sub-systems mounted on a common manifold.

Yet another objective of the present invention is to provide a surgical system for controlling pneumatic surgical devices.

Yet another objective of the present invention is to provide a surgical system for controlling pneumatic surgical devices having integral accumulators for storing extra pressurized air.

These and other advantages and objectives of the present invention will become apparent from the detailed description, drawings and claims that follow.

DETAILED DESCRIPTION OF THE PREFERRED EMBODIMENTS

Figure 1:
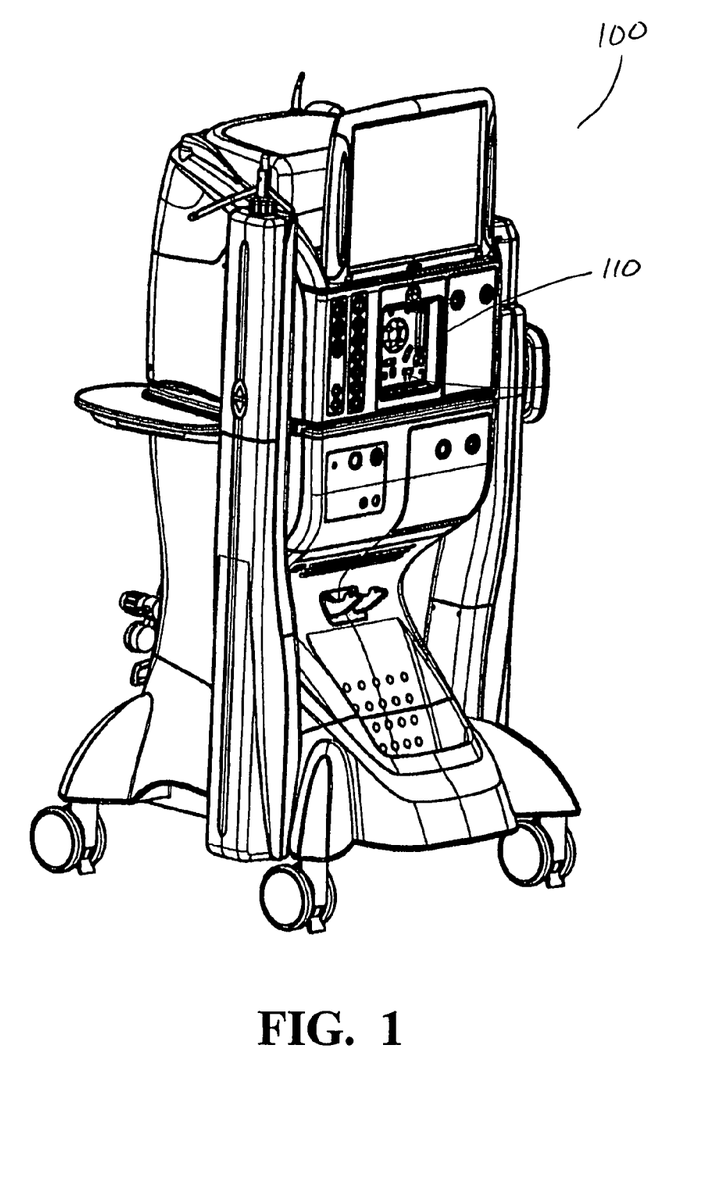
FIG. 1 is a front perspective view of a surgical console that may use the integral pneumatic manifold of the present invention.
Figure 2:
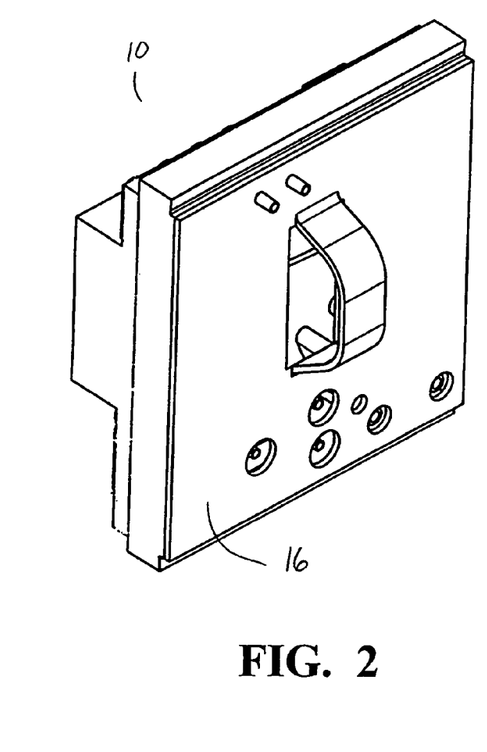
FIG. 2 is a front perspective view of a cassette that may be used with the present invention.
Figure 3:
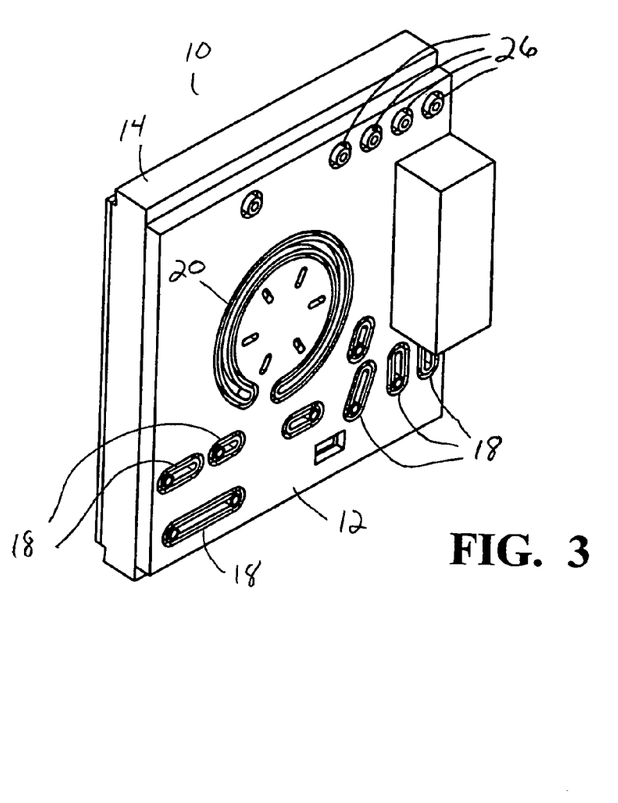
FIG. 3 is a rear perspective view of a cassette that may be used with the present invention.

As best seen in FIGS. 1, 2 and 3, cassette 10 that may be used with the present invention generally included valve plate 12, body 14 and cover 16. Valve plate 12, body 14 and cover 16 may all be formed of a suitable, relatively rigid, and thermoplastic. Valve plate 12 contains a plurality of openings 18 and pumping channel 20 that are sealed fluid tight by elastomers, forming a plurality of fluid paths. Ports 26 provide connectors between cassette 10 and surgical console 100 for the various irrigation and aspiration (pneumatic) functions of cassette 10 when cassette 10 is installed in cassette receiving portion 110 of console 100.

Figure 4:
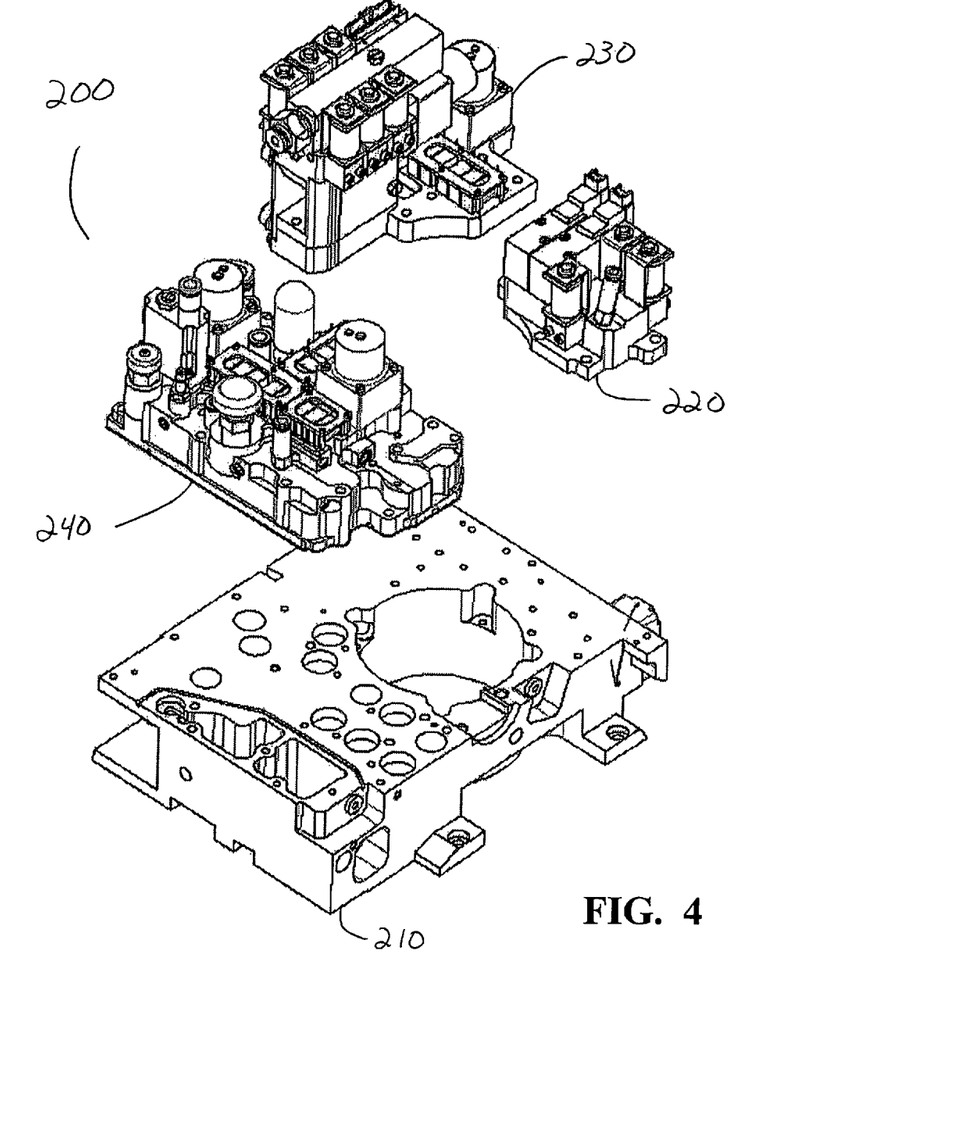
FIG. 4 is an exploded perspective view of the integral pneumatics manifold of the present invention.
Figure 5:
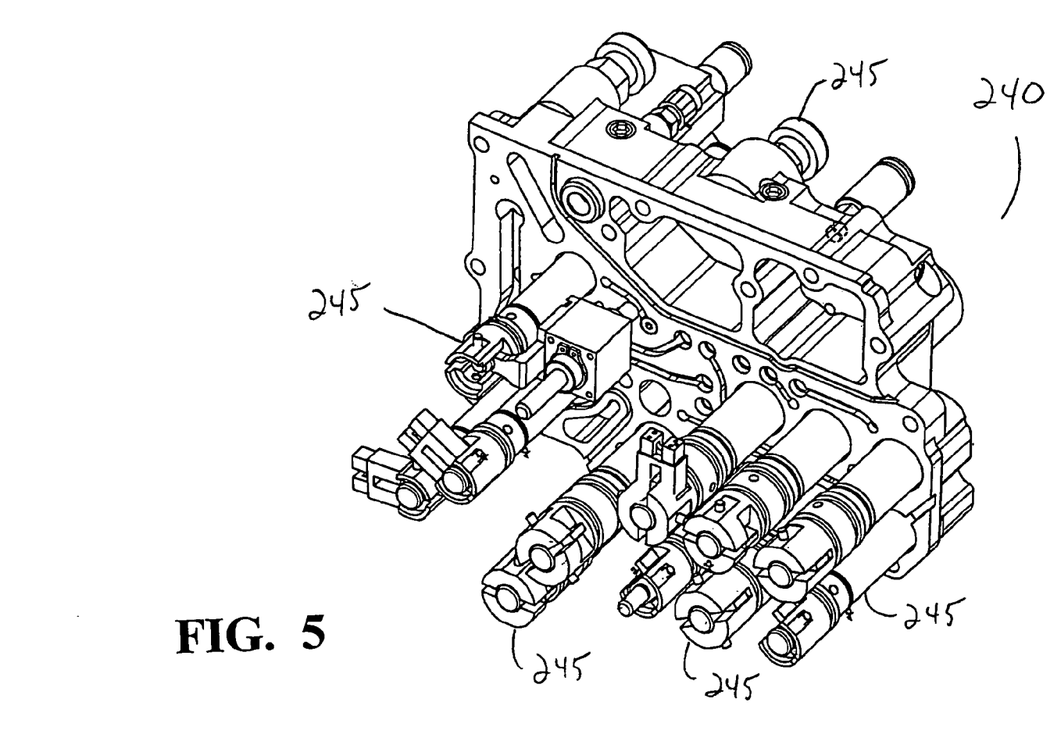
FIG. 5 is a perspective view of the valve or pincher manifold of the present invention and illustrating several active mechanical elements mounted on the manifold.

As best seen in FIG. 4, manifold assembly 200 contains a plurality of sub-assemblies or manifolds mounted to common primary manifold 210. For example, manifold assembly 200 may additionally contain aspiration manifold 220, and/or infusion/irrigation manifold 230 and/or valve or pincher manifold 240. As seen in FIG. 5, for example, each of manifolds 210, 220, 230 and 240 (manifold 240 used as an illustrative example) are self-contained, and may contain necessary the valves, regulators, sensors or other active embedded mechanical, electrical or electromechanical devices required to perform each manifold's primary function, such as air cylinders 245, by way of example. Manifolds 220 and 230 pneumatically and fluidly communicate with cassette 10 through primary manifold 210, and communication between the patient and cassette 10 is controlled by pincher manifold 240. Primary manifold 210 may be mounted in cassette receiving portion 110 of console 100 so that cassette 10 may be fluidly coupled to primary manifold 210. Primary manifold 210 may additionally contain pumps and fluid level and/or fluid flow sensors (all not shown).

Such a construction allows for the separation of the primary functionalities of each sub-assembly onto specific manifolds, thereby providing convenient and fast assembly, troubleshooting and repair. In addition, such a construction eliminates most of the various tubings and tubing connectors used in the prior art to connect the various components in each sub-assembly and reduces the overall size of the completed assembly.

Figure 6A:
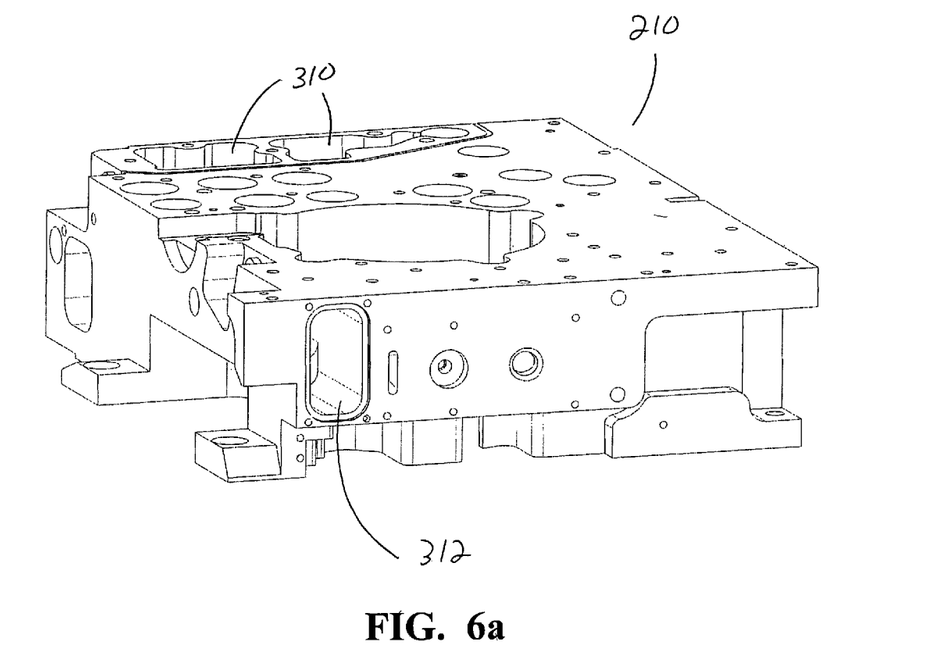
FIGS. 6a-6b are perspective views of manifolds that may be used with the present invention.
Figure 6B:
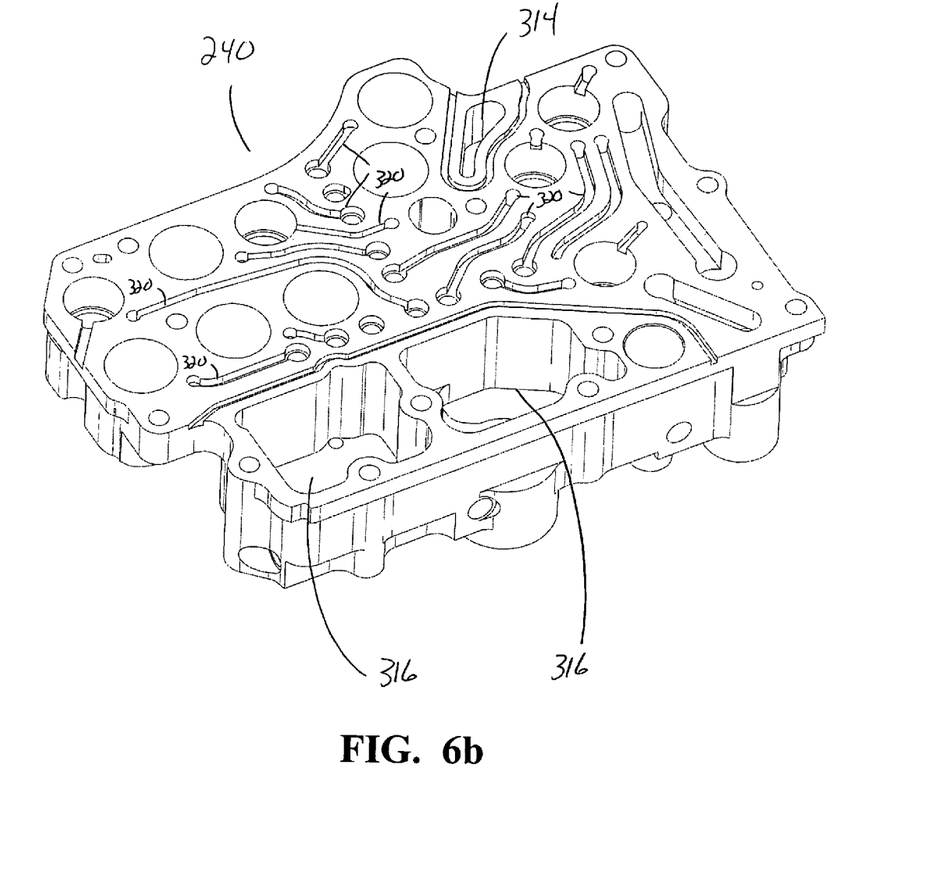

As best seen in FIG. 6a, primary manifold 210 contains pneumatic accumulators 310 and 312, which store pressurized air for infusion and reflux pressure, respectively. As seen in FIG. 6b, pincher manifold 240 contains pneumatic accumulators 314 and 316, which store pressurized air associated with a low pressure air source (not shown). As can also been seen in FIG. 6b, pincher manifold 240 contains a plurality of air passages 320 for directing pressurized air within pincher manifold 240 and among manifolds 210, 220, 230 and the valves, regulators, sensors or other active embedded mechanical, electrical or electromechanical devices required to perform each manifold's primary function, such as air cylinders 245. Accumulators 310, 312, 314 and 316 are illustrative examples only, and one skilled in the art will recognize that similar accumulators may be contained in any or all of manifolds 210, 220, 230 and 240. Accumulators 310, 312, 314 and 316 are integrally formed in their respective manifolds in otherwise unused portion of manifolds 210, 220, 230 and 240. Such a construction provides additional pressurized air storage for use in the event of power loss in a compact, reliable manner.

This description is given for purposes of illustration and explanation. It will be apparent to those skilled in the relevant art that modifications may be made to the invention as herein described without departing from its scope or spirit.

We claim:

1. An ophthalmic surgical system comprising:
   a) a cassette receiving portion adapted to receive a cassette for managing irrigation and aspiration fluid flows;
   b) a common primary fluidics and pneumatics manifold in the cassette receiving portion of the ophthalmic surgical system comprising a plurality of fluid passages through the primary manifold configured to fluidically couple directly to a surgical cassette;
   c) an infusion manifold mounted on the primary manifold comprising a plurality of fluid passages through the infusion manifold; and
   d) a first pneumatic accumulator integrally formed in at least one of the primary or infusion manifolds outside of and not directly connected to the respective plurality of fluid passages in the at least one manifold, the first pneumatic accumulator configured to fluidically couple directly to the fluid passages of the other of the primary or infusion manifolds.

2. The surgical system of claim 1 further comprising an aspiration manifold and a pincher manifold, both mounted to the primary manifold, and the aspiration manifold and the infusion manifold pneumatically communicate with each other through the pincher manifold.

3. The surgical system of claim 2 wherein the aspiration manifold and the infusion manifold fluidly communicate with each other through the primary manifold.

4. The surgical system of claim 2 wherein the aspiration manifold, the infusion manifold and the pincher manifold fluidly communicate with each other through the primary manifold.

5. The surgical system of claim 2 wherein the aspiration manifold and the infusion manifold fluidly communicate with each other through a cassette.

6. The surgical system of claim 1 further comprising at least one active embedded device mounted on the infusion manifold and/or the primary manifold.

7. The surgical system of claim 2 further comprising at least one active embedded device mounted on the aspiration manifold and/or the infusion manifold and/or the pincher manifold.

8. The surgical system of claim 2 further comprising at least one active embedded device mounted on the aspiration manifold and/or the infusion manifold and/or the pincher manifold and/or the primary manifold.

9. The surgical system of claim 2 further comprising a second pneumatic accumulator in at least one of the aspiration manifold or the pincher manifold.

10. An ophthalmic surgical system comprising:
    a) a cassette receiving portion adapted to receive a cassette for managing irrigation and aspiration fluid flows, comprising:
    b) a common primary fluidics and pneumatics manifold in a cassette receiving portion of the ophthalmic surgical system comprising a plurality of fluid passages through the primary manifold configured to fluidically couple directly to a surgical cassette;
    c) a pincher manifold mounted on the primary manifold and pneumatically communicating with the primary manifold system comprising a plurality of fluid passages through the pincher manifold; and
    d) a first pneumatic accumulator integrally formed in at least one of the primary or pincher manifolds outside of and not directly connected to the respective plurality of fluid passages in the at least one manifold, the first pneumatic accumulator configured to fluidically couple directly to the fluid passages of the other of the primary or pincher manifolds.

11. The surgical system of claim 10 further comprising an aspiration manifold and an infusion manifold, both mounted to the primary manifold, and the aspiration manifold and the infusion manifold pneumatically communicate with each other through the pincher manifold.

12. The surgical system of claim 11 wherein the aspiration manifold and the infusion manifold fluidly communicate with each other through the primary manifold.

13. The surgical system of claim 11 wherein the aspiration manifold, the infusion manifold and the pincher manifold fluidly communicate with each other through the primary manifold.

14. The surgical system of claim 11 wherein the aspiration manifold and the infusion manifold fluidly communicate with each other through a cassette.

15. The surgical system of claim 10 further comprising at least one active embedded device mounted on the pincher manifold and/or the primary manifold.

16. The surgical system of claim 11 further comprising at least one active embedded device mounted on the aspiration manifold and/or the infusion manifold and/or the pincher manifold.

17. The surgical system of claim 11 further comprising at least one active embedded device mounted on the aspiration manifold and/or the infusion manifold and/or the pincher manifold and/or the primary manifold.

18. The surgical system of claim 11 further comprising a second pneumatic accumulator in at least one of the aspiration manifold or the infusion manifold.

19. An ophthalmic surgical system comprising:
    a cassette receiving portion adapted to receive a cassette for managing irrigation and aspiration fluid flows;
    a common primary fluidics and pneumatics manifold in the cassette receiving portion of the ophthalmic surgical system comprising a plurality of fluid passages through the primary manifold configured to fluidically couple directly to a surgical cassette;

an infusion manifold mounted on the primary manifold comprising a plurality of fluid passages through the infusion manifold; and a pneumatic accumulator integrally formed in at least one of the primary or infusion manifolds outside of the respective plurality of fluid passages in the at least one manifold.

20. The surgical system of claim 1 further comprising an aspiration manifold and a pincher manifold, both mounted to the primary manifold, and the aspiration manifold and the infusion manifold pneumatically communicate with each other through the pincher manifold.

* * * * *